(12) United States Patent
Cowan

(10) Patent No.: US 6,403,777 B1
(45) Date of Patent: Jun. 11, 2002

(54) METALLOLIGANDS FOR CLEAVING NUCLEIC ACIDS

(75) Inventor: James A. Cowan, Lewis Center, OH (US)

(73) Assignee: The Ohio State University Research Foundation, Columbus, OH (US)

(*) Notice: Subject to any disclaimer, the term of this patent is extended or adjusted under 35 U.S.C. 154(b) by 0 days.

(21) Appl. No.: 09/348,225

(22) Filed: Jul. 6, 1999

(51) Int. Cl.[7] .......................... C07H 15/00; C12P 19/44
(52) U.S. Cl. ...................... 536/16.8; 536/4.1; 536/13.1; 536/13.2; 536/13.6; 536/14; 536/16.6; 536/25.4; 536/25.41; 536/25.42; 536/55.1; 536/55.3; 536/101; 536/121; 536/124; 435/74; 435/81; 435/82; 435/83; 549/230; 549/273; 549/414; 549/415
(58) Field of Search ................................ 536/4.1, 25.4, 536/25.41, 25.42, 55.1, 55.3, 101, 13.1, 13.2, 13.6, 14, 16.6, 168, 121, 124; 549/230, 414, 273, 415; 435/74, 81, 82, 83

(56) References Cited

U.S. PATENT DOCUMENTS 5,665,890 A * 9/1997 Jacobsen et al.
5,929,232 A * 7/1999 Jacobsen et al.

FOREIGN PATENT DOCUMENTS

WO        WO 00/01797       *   1/2000

OTHER PUBLICATIONS

"Efficient catalytic cleavage of DNA mediated by metalloaminoglycosides" by Sreedhara, et al., *Chem. Cummun.* 1998, pp. 1737–1738.
"Novel reagents for targeted cleavage of RNA sequences: towards a new family of inorganic pharmaceuticals" by Sreedhara, et al., *Chem. Commun.*, 1998, pp. 1147–1148.
"Specific binding of aminoglycoside antibiotics to RNA" by Wang, et al., *Chemistry & Biology*, May 1995, 2:281–290.
"Small Molecules That Selectively Block RNA Binding of HIV–1 Rev Protein Inhibit Rev. Function and Viral Production" by Zapp, et al., *Cell*, vol. 74, Sep. 24, 1993, pp. 939–978.

* cited by examiner

Primary Examiner—James O. Wilson
(74) Attorney, Agent, or Firm—Calfee, Halter & Griswold LLP

(57) ABSTRACT

Transition metal complexes, referred to hereinafter as "metalloligands", that catalyze the degradation of DNA and the cleavage of RNA at select sites are provided. In one embodiment, the metalloligand has the following structure:

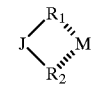

wherein R1 is an amino group, i.e. an NH, or an alkylamino group comprising 1 or 2 carbon atoms; wherein R2 is selected from the group consisting of an amino group, a hydroxyl group, i.e., O(H), an alkylamino group comprising 1 or 2 carbon atoms; and an alkylhydroxyl group comprising 1 or 2 carbon atoms; wherein J is a ligand which comprises at least one carbon-containing five-membered or six-membered ring structure; and wherein M is a transition metal ion which is bound via coordinate bonds to R1 and R2.

In another embodiment the metalloligand has the following structure:

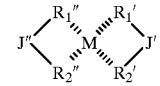

wherein R1' and R1" are the same or different and wherein R1' and R1" are an amino group or an alkylamino group comprising 1 or 2 carbon atoms; wherein R2' and R2" are the same or different and wherein R2' and R2" are selected from the group consisting of an amino group, a hydroxyl group, an alkylamino group comprising 1 or 2 carbon atoms, and an alkylhydroxyl group comprising one or two carbon atoms; wherein J' and J" are the same or different and wherein J' and J" are ligands which comprise at least one carbon-containing five-membered or six-membered ring structure; and wherein M is a transition metal ion which is bound via coordinate bonds to R1', R1", R2' and R2".

Methods of cleaving nucleic acids using the metalloligands are also provided.

23 Claims, 1 Drawing Sheet

METALLOLIGANDS FOR CLEAVING NUCLEIC ACIDS

This application claims the benefit of U.S. Provisional Application No. 60/192,862, which has a filing date of Jul. 6, 1998.

This invention was made in part with government support under CHE97069 awarded by the National Science Foundation. The U.S. government has certain rights in the invention.

BACKGROUND

At present in vitro degradation of nucleic acids is accomplished using enzymes known as nucleases. Nucleases which catalyze random scission of DNA and RNA are referred to, respectively, as DNases and RNases. DNases and RNases are used to purify and isolate proteins from cellular extracts Unfortunately, nucleases are not stable at ambient temperature, much less at physiological temperatures. Moreover, nucleases are sensitive to phosphate, and, thus, are not useful for cleaving nucleic acids in solutions comprising phosphate ions.

DNAses are also used to footprint DNA, i.e., to map those regions of isolated DNA that act as binding sites for proteins or peptides that function as transcription factors. However, DNases are relatively large macromolecules and, therefore, cannot identify the exact point of contact between the protein and the substrate DNA. Attempts have been made to overcome this problem of poor resolution by developing smaller molecules such as for example iron EDTA and copper dimethylphenanthroline, both of which are capable of catalyzing the cleavage of nucleic acids, particularly DNA. However, these small molecules produce reactive species which are diffusible and which may chemically react non-specifically, thereby leading to removal of the bases from the DNA molecule.

Furthermore, RNases are not selective, i.e., they do not preferentially catalyze cleavage of any particular RNA structure or sequence. Accordingly, RNases are not useful to characterize the secondary and tertiary structures RNA molecules assume in solution and, thus, they cannot be used to identity those RNA regions with which transcription factors and translation factors are believed to interact.

Thus, it is desirable to have new compounds and methods for catalyzing the cleavage of nucleic acids.

SUMMARY OF THE INVENTION

The present invention provides soluble transition metal complexes, referred to hereinafter as "metalloligands", that catalyze the degradation of DNA under hydrolytic conditions or mild oxidative conditions. Advantageously, the metalloligands also selectively catalyze the cleavage of RNA in regions of secondary and tertiary structure. In one embodiment, the metalloligand has the following structure:

wherein $R_1$ is an amino group, i.e. an NH, or an alkylamino group comprising 1 or 2 carbon atoms; wherein $R_2$ is selected from the group consisting of an amino group, a hydroxyl group, i.e., O(H), an alkylamino group comprising 1 or 2 carbon atoms; and an alkylhydroxyl group comprising 1 or 2 carbon atoms; wherein J is a ligand which comprises at least one carbon-containing five-membered or six-membered ring structure; and wherein M is a transition metal ion which is bound via coordinate bonds to $R_1$ and $R_2$.

In another embodiment the metalloligand has the following structure:

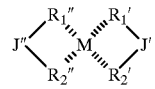

wherein $R_1'$ and $R_1''$ are the same or different and wherein R1 ' and R1" are an amino group or an alkylamino group comprising 1 or 2 carbon atoms; wherein R2' and R2" are the same or different and wherein R2' and R2" are selected from the group consisting of an amino group, a hydroxyl group, an alkylamino group comprising 1 or 2 carbon atoms, and an alkylhydroxyl group comprising one or two carbon atoms; wherein J' and J" are the same or different and wherein J' and J" are ligands which comprise at least one carbon-containing five-membered or six-membered ring structure; and wherein M is a transition metal ion which is bound via coordinate bonds to R1', R1", R2' and R2".

The present invention also relates to methods of making the metalloligands. The present invention also relates to methods of using the metalloligands to catalyze the cleavage or degradation of DNA and to catalyze the cleavage of RNA at select sites, i.e. at sites which assume a certain secondary and tertiary structural motif when the RNA is in solution.

DETAILED DESCRIPTION OF THE INVENTION

Figure 1:
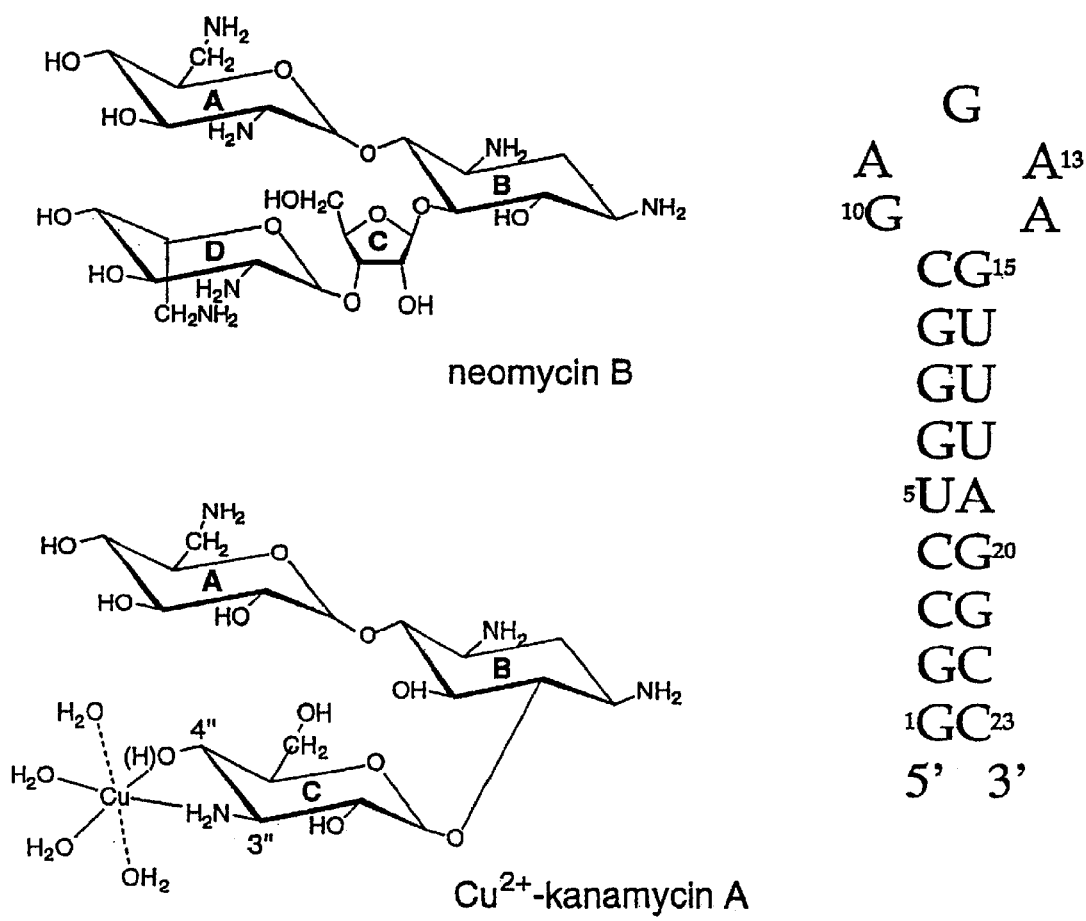
FIG. 1 depicts the structures of the metalloligand, $Cu^{2+}$-kanamycin A, the aminoglycoside neomycin B, and the structure of a 23-mer RNA aptamer, hereinafter termed "R23", which has a high binding affinity for neomycin B.

The present invention provides soluble transition metal complexes, referred to hereinafter as "metalloligands", that are useful for degrading DNA under hydrolyzing conditions and mild oxidizing conditions and for cleaving RNA at select sites. As used herein, oxidizing conditions refers to conditions in which the reaction solution, whether it be in vitro or in vivo, contains a source of electrons, such as for example ascorbate or $H_2O_2$ and an activated or activatable dioxygen, such as for example $H_2O_2$ or $O_2$. Mild oxidizing conditions are those in which no cleavage of the DNA substrate or RNA substrate occurs unless a metalloligand is present.

In accordance with the present invention, the metalloligand is, preferably, a non-proteinaceous compound that comprises a transition metal and at least one ligand comprised of at least one five-membered or six-membered ring structure. In one embodiment the metalloligand has the following structure:

wherein R1 is an amino group or an alkylamino group comprising 1 or 2 carbon atoms; wherein R2 is selected from the group consisting of an amino group, a hydroxyl group, an alkylamino group comprising 1 or 2 carbon atoms, and an alkylhydroxyl group comprising 1 or 2 carbon atoms; wherein J is a ligand which comprises at least one carbon-containing five-membered or six-membered ring structure; and wherein M is a transition metal ion which is bound via a coordinate bond to R1 and R2.

Preferably, the J ligand comprises a chain of from 2 to about 5, five-membered or six-membered ring structures which are connected by glycosidic or ether linkages. Suitable five-membered and six-membered ring structures are cyclopentanes, cyclohexanes, as wells as rings formed from monosaccharides such as for example, glucose, mannose, galactose, and ribose. Preferably each ring structure comprises one or more amino groups or one or more alkylamino groups. More preferably, each ring structure further comprises one or more hydroxyl groups or one or more alkyl-hydroxyl groups. Most preferably, the J ligand is an aminoglycoside which comprises from 2 to about 5 sugar rings connected by glycosidic linkages. The aminoglycosides neomycin B, paramomycin, kanamycin A, kanamycin B, tobramycin, neamine and streptomycin, which are representative examples of suitable J ligands, have the following structures:

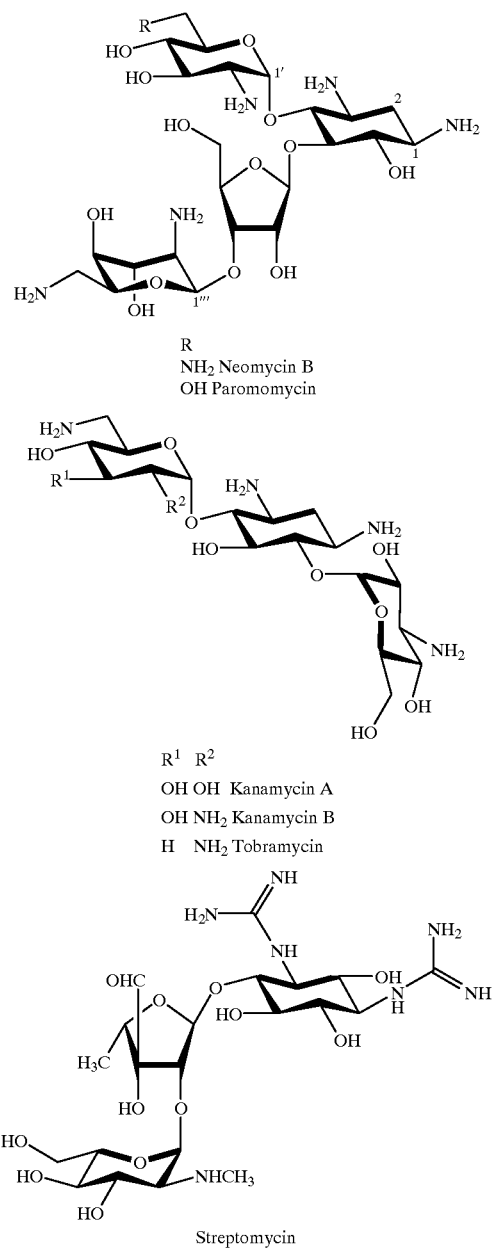

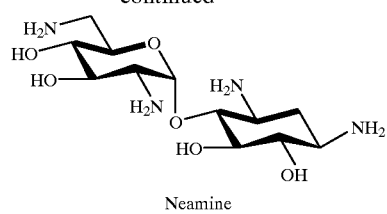

Neamine

Other suitable aminoglycosides are gentamycin $C_1$, gentamycin $C_2$, and gentamycin $C_{14}$, ribostamycin and lividomycin.

Although R1 and R2 may be attached to different ring structures of the J ligand, it is preferred that R1 and R2 be attached to adjacent carbon atoms of the same five-membered or six-membered ring structure. To increase the stability of the metalloligand, it is preferred that R1 and R2 both be in an equatorial conformation. Preferably the transition metal ion is a first row transition metal, more preferably $Cu^{1+}$ or $Cu^{2+}$.

The structure of two preferred metalloligands, $Cu^{2+}$(neamine) and $Cu^{2+}$(kanamycin A) are shown below:

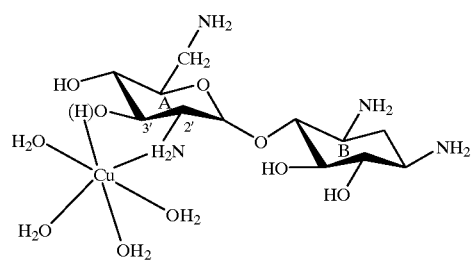

$Cu^{2+}$-neamine

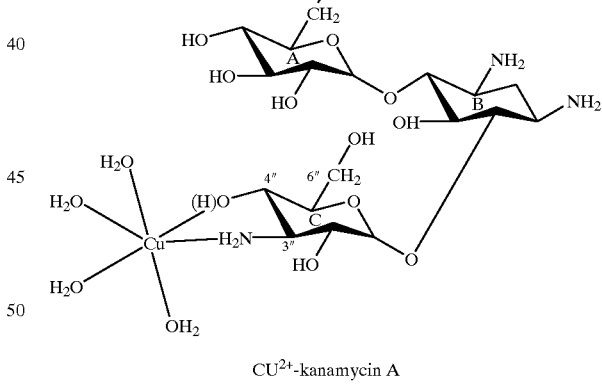

$CU^{2+}$-kanamycin A

In another embodiment, the aminoglycoside has the following structure:

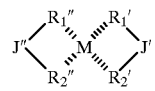

wherein R1' and R1" are the same or different and wherein R1' and R1" are an amino group or an alkylamino group comprising 1 or 2 carbon atoms; wherein R2' and R2" are the same or different and wherein R2' and R2" are selected from the group consisting of an amino group, a hydroxyl group, an alkylamino group comprising 1 or 2 carbon atoms, and an alkylhydroxyl group comprising one or two carbon atoms; wherein J' and J" are the same or different and wherein J' and J" are ligands which comprise at least one carbon-containing five-membered or six-membered ring structure; and wherein M is a transition metal ion which is bound via coordinate bonds to R1' , R1" , R2' and R2".

Advantageously, the metalloligands catalyze the degradation of DNA under conditions of physiological pH and ionic strength and at temperatures ranging from about 4° C. to about 40° C. Moreover, the present metalloligands catalyze the degradation of DNA under conditions where the concentration of metalloligand required is significantly lower, i.e., from about $10^3$ to about $10^9$ fold lower than the concentration of the substrate. Accordingly, the metalloligands, particularly, the metalloaminoglycosides, are useful laboratory tools for purifying proteins from mixtures, such as, for example, cellular extracts, which contain proteins and nucleic acids.

The present metalloligands also catalyze the linearization of circular DNA, such as for example, plasmid DNA, or supercoiled DNA. Accordingly, the metalloligands are also useful laboratory tools for preparing nucleic acids molecules isolated from bacteria for further processing.

The present metalloligands also catalyze the selective cleavage of RNA molecules that comprise secondary and tertiary structural motifs. Accordingly, the present metalloligands are useful for inactivating RNA molecules which have such secondary and tertiary structural motifs. Further the metalloligands are useful for identifying those regions of the RNA which are involved in forming such secondary and tertiary structural motifs.

Preparation of the Metalloligand

The present metalloligands are prepared by adding a soluble J ligand, such as for example, an aminoglycoside antibiotic, to a solution comprising a soluble salt of the transition metal. Preferably, the molar ratio of transition metal salt to J ligand is from about 2:1 to 1:2. The resulting mixture is then agitated or refluxed until the metalloligand is formed. Preferably, formation of the metalloligand is confirmed by thin layer chromatography. Then the resulting metalloligand is isolated from the solution, either by filtration if a non-aqueous solution is used or by precipitation if an aqueous solution is used.

Preferably, the metalloligand is precipitated from an aqueous solution by adding an equivalent volume of a solvent that is miscible with water but less polar than water. The solvent is preferably an alkyl alcohol, more preferably ethyl alcohol. The precipitate is then collected, and preferably washed exhaustively with the solvent, dissolved in water, and precipitated a second time with the solvent.

Cleaving DNA with a Metalloligand

A. Linearization of Supercoiled DNA or Plasmid DNA

Supercoiled DNA, such as, for example, DNA isolated from bacteria or plasmid DNA, preferably at a concentration of from about 0.1 µM to about 100 µM (base pairs), is reacted in a buffered solution, preferably a HEPES-buffered solution, with a metalloligand at submicromolar concentrations of from about 1 nM to about 10 nM to produce linearized double stranded DNA. To enhance the rate of degradation, it is preferred that the reaction be performed under oxidizing conditions. Oxidizing conditions are achieved, for example, by adding a reducing agent such as, for example, sodium ascorbate to an aerobic reaction mixture, i.e., a reaction mixture which contains dissolved oxygen. The reaction time is inversely related to the temperatures employed. If desired, the linearized double-stranded DNA is further processed and used to produce RNA molecules by conventional techniques, such as by in vitro transcription of the linearized DNA. If desired, the linearized double-stranded DNA is used as a laboratory tool, such as a molecular weight marker in gel electrophoresis.

B. Footprinting DNA

A sample of the DNA desired to be footprinted, preferably a sample comprising DNA segments radioactively labeled at their 5' ends, is reacted with a metalloligand in an aqueous solution at physiological pH, ionic strength, and temperature. The concentration of metalloligand in the solution and the reaction time are adjusted so that the metalloligand cleaves each segment in the sample at only one or a few sites. Then, a second sample of the DNA, preferably a sample comprising DNA segments radioactively labeled at their 5' ends, is combined with the protein of interest and treated with the metalloligand under the same reaction conditions. Both sets of cleavage fragments are separated on an electrophoretic gel. The gels for each sample are then compared to identify the position of missing fragments, i.e., the fragments protected or blocked by the protein of interest. The sequence of the protected fragments is determined on a sequencing gel made from the same DNA sample.

Catalyzing the Cleavage of RNA with Metalloligands

A. Catalyzing the Cleavage of RNA with Known J Ligand Binding Sites

RNA having a secondary structural motif or tertiary structure which binds to a J ligand is cleaved by reacting such RNA with a metalloligand having such J ligand. Preferably, a metalloligand whose J ligand binds with tight affinity to the secondary or tertiary structure of the RNA is used. Recent reports have demonstrated selective and high affinity binding of aminoglycosides to a variety of secondary structural motifs such as for example regions of duplex structure which may be distorted due to base mismatches, bulges, pseudoknots, and hairpins. In particular, Neomycin B and other 2-deoxystreptamine containing aminoglycosides have been reported to bind to 16S rRNA, 23 S rRNA, group I introns and hammerhead ribozyme. Neomycin B also binds to the purine rich internal loop of the human immunodeficiency virus (HIV) rev response element (RRE) and to the TAR region of the HIV genome.

The metalloligand is added to a sample containing substrate RNA with the recognized binding motif. Preferably, the RNA is in an aqueous solution having a pH of from about 7 to about 8. Preferably, the reaction is conducted at a temperatures ranging from 4° C. to about 40° C. The amount of time required to achieve cleavage is inversely related to the temperature. Good results have been achieved when 10 nmol Cu(kanamycin) was incubated with a structured 23 mer RNA having the sequence 5'-GGCCUGGGCGAGAAGWUUAGGCC-3' in an aqueous solution having a pH of 7.3 at a temperature of 37° C. and a reaction time of 90 minutes. As shown in FIG. 1, the 23 mer substrate RNA has a stem-loop motif which is selectively cleaved by the metalloligand.

B. Mapping RNA 2° and 3° Structure with Metalloligands

Complex RNA molecules are characterized, i.e. regions which assume secondary and tertiary structural motifs are identified, by reacting such RNA molecules with metalloligands whose J ligands are known to bind to secondary and tertiary structural motifs. The metalloligand preferably at a final concentration of about 100 picomole to about 100 nanomole, and the substrate RNA, preferably at a concentration of from about 1 µM to about 100 µM (bases), are combined in a solution, preferably an aqueous solution at a pH of from about 7 to about 8. Preferably, the solution has an ionic strength of 10 mM to about 50 mM. Preferably, the reaction is conducted at a temperature of from about 4° C. to 40° C. Following the reaction the RNA is isolated from the solution and assayed to determine if cleavage has occurred. Preferably, cleavage of the RNA is assayed by conventional methods such as for example FPLC and gel electrophoresis of the resulting reaction products. Cleavage of the RNA into two or more fragments indicates that the substrate RNA contains one or more secondary structural motifs that are recognized by the J ligand of the metalloligand. The resulting fragments are then sequenced to identify the sequences flanking to the cleavage site, and to thereby identify the RNA region or regions which are involved in forming secondary structure and tertiary structure when the RNA is present in a physiological solution. Preferably, the substrate RNA is reacted with a panel of metalloligands whose J ligands recognize and bind to different secondary structural motifs to obtain a more complete structural map of the substrate RNA. Such information is useful for characterizing the folding pattern and the tertiary structure of the substrate RNA in a physiological solution.

Purifying Proteins from Mixtures Comprising Nucleic Acids and a Protein of Interest Proteins are separated from mixtures comprising proteins and nucleic acids using metalloligands. The mixture is combined with a metalloligand, preferably at a concentration from about 0.5 $\mu$M to 5 $\mu$M, and incubated, preferably, at a temperature of from about 4° C. to about 40° C., for a time sufficient to allow cleavage of the nucleic acids into low molecular weight nucleotides and oligonucleotides. The solutions, e.g., cell extracts, are reacted with the metalloligand at physiological pH and ionic strength. Thereafter, the proteins in the solution are separated from the low molecular weight components using conventional techniques, such as molecular sieve chromatography, dialysis, or centrifugation through a membrane with a cut-off point below the molecular weight of the desired protein and above the molecular weight of the nucleic acid cleavage products.

EXAMPLE 1

Cu(kanamycin A)

To kanamycin A sulfate (0.1455 g, .0.25 mmol) in 5 mL water was added $CuSO_4$ (0.0624 g, 0.25 mmol). The reaction was stirred at room temperature for 24 h resulting in a blue colored solution. Ethanol (5 mL) was added to the reaction mixture to provide a blue solid, which was filtered from the solution, washed twice in EtOH by stirring for 6 h each time, dissolved in water and EtOH precipitated to give a pure Complex 1. TLC was carried out with a mixed solvent system of Proponal:Acetone:20% aqueous $NH_4OAc:NH_4OH$ (1:1:5:0.025) to give an $R_f$=0.33 for Complex 1 versus $R_f$=0.60 for kanamycin A sulfate. Elemental analysis for $[(C_{18}H_{38}N_4O_{11}Cu)(SO_4)_2]7H_2O$, calculated (observed): C, 24.89 (24.56); H, 5.99 (5.08); N, 6.24 (6.18). UV-Vis (in water): $\lambda_{max}$ nm ($M^{-1}cm^{-1}$) 672 (130). EPR (15 K): $g_{parallel}$ 2.514, $g_{perp}$ 2.045.

EXAMPLE 2

Cu(kanamycin A)$_2$,

To kanamycin A sulfate (0.291 g, 0.5 mmol) in 5 mL water was added $CuSO_4$ (0.0624 g, 0.25 mmol). The reaction was stirred at 40° C. for 12 h resulting in a green colored solution. A dark green complex was isolated and purified from the reaction solution as described above for the metalloligand of example 1. TLC was carried out with a mixed solvent system of Proponal:Acetone:20% aqueous $NH_4OAc:NH_4OH$ (1:1:5:0.025) to give an $R_f$=0.30 for Complex 2. Elemental analysis for $[(C_{36}H_{76}N_8O_{22}Cu)(SO_4)_3]$ $8H_2O$, calculated 29.43 (29.65); H, 6.27 (6.34); N, 7.63 (7.13). UV-Vis (in water): $\lambda_{max}$ nm ($M^{-1}cm^{-1}$) 612 (430). EPR (15 K): $g_{parallel}$ 2.459, 2.306, $g_{perp}$ 2.023.

EXAMPLE 3

Cu(neomycin B)

To neomycin (0.227 g, 0.25 mmol) in 5 mL water was added $CuSO_4$ (0.0624 g, 0.25 mmol). The reaction was stirred at 40° C. for 12 h resulting in a pale blue colored solution. A pale blue solid complex was isolated and purified from the reaction solution as described above for the metalloligand of example 1. TLC was carried out with a mixed solvent system of Proponal:Acetone:20% aqueous $NH_4OAc:NH_4OH$ (1:1:5:0:025) to give an $R_f$=0.17 for Complex 3 versus $R_f$=0.45 for neomycin. Elemental analysis for $[(C_{23}H_{50}N_6O_{13}Cu)(SO_4)_3]8H_2O$, calculated (observed): C, 24.78 (25.30); H, 5.92 (6.05); N, 7.54 (7.43). UV-Vis (in water): $\lambda_{max}$ nm ($\epsilon$, $M^{-1}cm^{-1}$) 712 (65).

EXAMPLE 4

Cu(neamine)

Neamine hydrochloride was synthesized as described in Grapsas, I.; Cho, Y.; Moshaberry, S. *J. Org. Chem.* 1994, 59, 1918, which is specifically incorporated herein by reference. To neamine hydrochloride (0.6015 g, 1.31 mmol) in 60 mL MeOH was added $Cu(OAc)_2$ (0.2601 g, 1.31 mmol) and the solution was brought to reflux. A light green-blue precipitate was observed immediately, and the reaction was allowed to reflux for 48 h then filtered. The solid blue product was washed and purified as described above for the metalloligand of example 1. Elemental analysis for $[(C_{12}H_{25}N_4O_6Cu)4H_2O4HCl]$, calc (observed) C, 23.90 (23.92); H, 6.14 (5.66); N, 9.29 (8.87). UV-Vis (in water): $\lambda_{max}$, nm ($M^{-1}cm^{-1}$)718 (44).

Stability of the Metalloligands of Examples 1–4

Purified Cu(kanamycin A) and Cu neamine are stable in aqueous solution for more than one day. Cu(kanamycin A)$_2$ and Cu(neomycin B) were less stable and formed precipitates within 4 hours. Thus, because of their stability in an aqueous solution, Cu(kanamycin A) and Cu neamine are preferred metalloligands.

EXAMPLE 5

Non-Specific DNA Cleavage using Metalloligands of Examples 1–4

Plasmid DNA (50 $\mu$M, bp) was added to a reaction solution containing 20 mM HEPES, pH 7.3 and reacted with Cu(kanamycin A) at a concentration of 1 $\mu$M and 500 nM . At least some DNA was nicked after only 5 minutes exposure to 500 nM of Cu(kanamycin A). The plasmid DNA substrate was completely degraded within 1 hour when reacted with 1 $\mu$M of Cu(kanamycin A). The addition of excess metal-free aminoglycoside inhibited cleavage. However, Cu(kanamycin A)-catalyzed DNA cleavage was not inhibited by the addition of super oxide dismutase (SOD), sodium azide ($NaN_3$), DMSO, EtOH to the reaction mixture. Moreover, Cu(kanamycin A)-catalyzed DNA cleavage was not inhibited when the reaction was performed under an argon atmosphere, i.e., under anaerobic conditions. These results indicate that Cu(kanamycin A)-catalyzed DNA cleavage occurs by a hydrolytic cleavage pathway. Thus, Cu(kanamycin A. can be used either in vivo or in vitro to cleave DNA in solutions that lack either dioxygen or a source of electrons.

Plasmid DNA (50 $\mu$M, bp) was also added to a solution containing, 10 mM HEPES, pH 7.3 and incubated with Cu(neamine) at concentrations ranging from 0.1 to 200 $\mu$M at 37° C. for various intervals of time. The appearance of open circular DNA (form II) and the disappearance of supercoiled DNA (form I) was monitored via gel electrophoresis. The appearance of form II was observed within less than one hour of incubation even when the solution contained low concentrations, i.e., 0.1 μmolar, of Cu(neamine).

Plasmid DNA was cleaved when reacted with of Cu(kanamycin A)$_2$ and Cu(neomycin B) at concentrations as low as 100 nM. Thus, DNA substrates can be cleaved using the metalloligands of examples 1–4. Moreover, cleavage can be achieved using catalytic concentrations (i.e., concentrations which are significantly lower than the concentration of the substrate of these metalloligands).

Metalloligands comprising the transition metal ions Fe, Mn, Co, and Ni were formed by mixing a 10 μM solution of the salts FeSO$_4$, MnCl$_2$, CoSO$_4$, and NiCi$_2$, and an equivalent volume of 10 μM kanamycin A for 12 h at 35° C. Complex formation was monitored by thin layer chromatography, using PrOH:Me$_2$CO:NH$_4$OAc (20%(aq)) (1:1:5:0.025) on silica gel plates. R$_f$ values were identified as follows: kanamycin A, 0.61; V-(kan A), 0.44; Fe-(kan A), 0.38; Mn-(kan A), 0.56; Co-(kan A), 0.47; Ni-(kan A). No complex formation was observed when 10 μM kanamycin A was incubated with a solution containing 10 μM ZnSO$_4$. Plasmid DNA (51.1 μM base pair concentration of pT7-7) was added to a solution containing 20 mM HEPES, pH 7.3 and 1 μM final concentration of each metal-kanamycin A complex and incubated for 1 hour. Little to no cleavage of the DNA substrate was observed under these conditions. Thus, metalloligands comprising the transitions metals Fe, Mn, Co, and Ni are less preferred than metalloligands comprising the transition metal copper.

EXAMPLE 6
Non-Specific DNA Cleavage using Metalloligands of Examples 1–4 under Oxidizing Conditions Plasmid DNA at a concentration of 50 μM, bp was added to a reaction solution containing 20 mM HEPES, pH 7.3, and the metalloligands of Examples 1–4 and the reducing agent ascorbic acid. Complete conversion of supercoiled DNA (51 μM base pair) to a linear form was observed with 5 nM of Cu(kanamycin A) in the presence of 10 μM ascorbate. Cleavage of the DNA did not occur when the reaction mixture lacked a metalloligand but contained Cu$^{2+}$ (aq) or Cu2+ and ascorbate. The metalloligands of examples 1 to 4 also degraded plasmid DNA completely in the presence of 10 μM H$_2$O$_2$.

DMSO and EtOH, which are hydroxy radical quenchers, did not inhibit oxidative DNA cleavage by Cu(kanamycin A). However, superoxide dismutase (SOD) and NaN$_3$ inhibited oxidative DNA cleavage mediated by Cu(kanamycin A). Accordingly, it is believed that activated oxygen species (such as O$_2^-$ $^{or\ 1}$O$_2$) are involved in plasmid cleavage when the metalloligand and the substrate DNA are reacted under oxidizing conditions.

EXAMPLE 7
Specific Cleavage of a 23 RNA using Metalloligands of Examples 1–4

R23 RNA (5'-GGCCUGGGCGAGAAGUUUAGGCC-3') which has a high binding affinity to neomycin B was combined with the metalloligands of Examples 1–4 in a reaction mixture containing 20 mM HEPES, pH 7.3. The combination of only 20 nM Cu(kanamycin A) with the 23-mer RNA (30 μM base pair) led to efficient hydrolysis (54%) after 90 minutes, as shown by FPLC analysis. Hydrolysis efficiency increased when 100 nM Cu(kanamycin A) was used instead of 20 nM. Similar results were obtained with Cu(kanamycin A)$_2$ and Cu(neomycin B). Combining purified Cu(kanamycin A) with linear oligo (A$_{12-18}$) or poly(C) under similar reaction conditions resulted in no cleavage, thereby demonstrating the requirement for secondary structure and or tertiary structure to effect cleavage.

EXAMPLE 8
Cleaving RNA at Select Sites under Oxidizing Conditions

Uniformly labeled R23 RNA was incubated at 37° C. for 1 hr with various concentrations of Cu(kanamycin A) in the presence and absence of the co-reactants H$_2$O$_2$ and ascorbate. Cleavage products were separated on a denaturing polyacrylamide gel. Two sites of cleavage were identified, one in the loop region at G$^{15}$ and the other in the stem region at C$^4$. These sites are depicted in FIG. 1. Addition of 100 μM ascorbate or 1 μM H$_2$O$_2$ to the reaction mixture resulted in an extremely efficient degradation of the target RNA with nanomolar concentrations of Cu(kanamycin A). RNA cleavage of 30% was observed by FPLC with 1 nM Cu(kanamycin A) after incubation at 37° C. for 1 hour. Cleavage efficiencies of approximately 25% were obtained for solutions containing 50 pM Cu(kanamycin A) and 100 μM ascorbate or 1 μM H$_2$O$_2$ following incubation for 2 h at 37° C. Thus, Cu(kanamycin A) is able to selectively cleave RNA at physiological pH and under mild oxidizing conditions.

Although specific embodiments of this invention have been shown and described, various adaptations and modifications can be made without departing from the scope of the invention as defined in the appended claims.

What is claimed is:

1. An isolated metalloligand having the following structure:

wherein
R$_1$ is an amino group or an alkylamino group comprising 1 or 2 carbon atoms;
R$_2$ is selected from the group consisting of an amino group, a hydroxyl group, an alkylamino group comprising 1 or 2 carbon atoms; and an alkylhydroxyl group comprising 1 or 2 carbon atoms;
J is a chain which comprises a plurality of carbon-containing five-membered or six-membered ring structures, wherein each of said ring structures is a monosaccharide, and wherein each of said ring structures has one or more amino groups or one or more alkylamino groups attached thereto; and
M is a transition metal ion which is bound via coordinate bonds to R$_1$ and R$_2$.

2. The metalloligand of claim 1 wherein J comprises two to 5 five-membered or six membered ring structures.

3. The metalloligand of claim 1 wherein R$_1$ and R$_2$ are attached to adjacent carbon atoms of the same ring structure.

4. The metalloligand of claim 3, wherein each of said ring structure further comprises one or more hydroxyl groups or one or more hydroxylamino groups.

5. The metalloligand of claim 1, wherein J comprises an aminoglycoside containing from two to five monosaccharides connected by glycosidic linkages.

6. The metalloligand of claim 1, wherein J is an aminoglycoside selected from the group consisting of neomycin B, paramomycin, kanamycin A, neamine, kanamycin B, tobramycin, streptomycin, gentamycin, ribostamycin, and lividomycin.

7. The metalloligand of claim 1, wherein M is a first row transition metal ion.

8. The metalloligand of claim 1, wherein M is $Cu^{1+}$ or $Cu^{2+}$.

9. The metalloligand of claim 1, wherein the metalloligand is a solid.

10. The metalloligand of claim 1, wherein said metalloligand is in a solution which lacks free ligand and free transition metal.

11. The metalloligand of claim 1 wherein M is $Cu^{1+}$ or $Cu^{2+}$ and J is an aminoglycoside.

12. The metalloligand of claim 11 wherein the aminoglycoside is neamine or kanamycin A.

13. A metalloligand having the following structure:

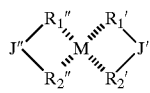

wherein:

$R_1'$ and $R_1''$ are the same or different;

$R_1'$ and $R_1''$ are an amino group or an alkylamino group comprising 1 or 2 carbon atoms;

$R_2'$ and $R_2''$ are the same or different;

$R_2'$ and $R_2''$ are selected from the group consisting of an amino group, a hydroxyl group, an alkylamino group comprising 1 or 2 carbon atoms, and an alkylhydroxyl group comprising one or two carbon atoms;

wherein J' and J'' are the same or different and wherein J' and J'' are chains which comprise a plurality of carbon-containing five-membered or six-membered ring structures, wherein each of said ring structures is a monosaccharide, and wherein each of said ring structures has one or more amino groups or one or more alkylamino groups attached thereto; and M is a transition metal ion which is bound via coordinate bonds to $R_1'$, $R_1''$, $R_2'$ and $R_2''$.

14. A method of preparing a metalloligand comprising the steps of:

(a) reacting a ligand and a soluble salt of a transition metal in an aqueous or non-aqueous solution for a time sufficient to form a complex between the transition metal and the ligand; wherein said ligand comprises the following structure

where $R_1$ is an amino group or an alkylamino group comprising 1 or 2 carbon atoms;

$R_2$ is selected from the group consisting of an amino group, a hydroxyl group, an alkylamino group comprising 1 or 2 carbon atoms, and an alkylhydroxyl group comprising 1 or 2 carbon atoms; and J is a chain which comprises a plurality of carbon-containing five-membered or six-membered ring structures, wherein each of said ring structures is a monosaccharide, and wherein each of said ring structures has one or more amino groups or one or more alkylamino groups attached thereto; and (b) isolating the complex from the solution.

15. A method of catalyzing the cleavage of nucleic acids comprising the steps of:

(a) providing a metalloligand of claim 1 or claim 13.

(b) administering the metalloligand to a sample containing the nucleic acid.

16. The method of claim 15 wherein the nucleic acid is in an aqueous solution having a pH of from about 7 to 8.

17. The method of claim 15, wherein the concentration of the metalloligand is at least 10 times lower than the concentration of the substrate.

18. The method of claim 17, wherein the concentration of the metalloligand is from about $10^3$ to about $10^9$ fold lower than the concentration of the nucleic acid substrate.

19. The method of claim 15 wherein the sample lacks a reducing agent or an activated dioxygen species.

20. The method of claim 15 wherein the sample comprises a reducing agent and an activated or activatable dioxygen species.

21. The method of claim 15, wherein the metalloligand has the following structure:

where $R_1$ is an amino group or an alkylamino group comprising 1 or 2 carbon atoms;

$R_2$ is selected from the group consisting of an amino group, a hydroxyl group, an alkylamino group comprising 1 or 2 carbon atoms, and an alkylhydroxyl group comprising 1 or 2 carbon atoms;

J is an aminoglycoside; and

M is $Cu^{1+}$ or $Cu^{2+}$.

22. The method of claim 21 wherein the aminoglycoside is kanamycin, neamine, or neomycin.

23. The method of claim 15 wherein the nucleic acid is RNA and wherein the metalloligand catalyzes cleavage of RNA regions involved in forming secondary structure and tertiary structure when the RNA is in a solution.

* * * * *

UNITED STATES PATENT AND TRADEMARK OFFICE
CERTIFICATE OF CORRECTION

PATENT NO. : 6,403,777 B1
DATED : June 11, 2002
INVENTOR(S) : James A. Cowan

It is certified that error appears in the above-identified patent and that said Letters Patent is hereby corrected as shown below:

Column 2,
Line 10, please replace "R1' and R1''" with -- $R_1'$ and $R_1''$ --.
Line 11, please replace "R2'" with -- $R_x'$ --.
Line 12, please replace "R2''" with -- $R_x''$ --.
Line 12, please replace "R2' and R2'" with -- $R_2'$ and $R_x'$ --.
Line 20, please replace "R1', R1'', R2' and R2''" with -- $R_1'$, $R_1''$, $R_x'$, $R_x''$ --.
Line 58, please replace "R1" with -- $R_1$ --.
Line 59, please replace "R2" with -- $R_2$ --.
Line 67, please replace "R1 and R2" with -- $R_1$ and $R_2$ --.

Column 4,
Line 14, please replace "R1 and R2" with -- $R_1$ and $R_2$ --.
Line 15, please replace "R1 and R2" with -- $R_1$ and $R_2$ --.
Line 18, please replace "R1 and R2" with -- $R_1$ and $R_2$ --.
Line 63, please replace "R1' and R1''" with -- $R_1'$ and $R_1''$ --.
Line 64, please replace "R1' and R1''" with -- $R_1'$ and $R_1''$ --.
Line 65, please replace "R2' and R2''" with -- $R_2'$ and $R_2''$ --.
Line 66, please replace "R2' and R2''" with -- $R_2'$ and $R_2''$ --.

Column 5,
Line 8, please replace "R1', R1'', R2' and R2''" with -- $R_1'$, $R_1''$, $R_x'$, $R_x''$ --.
Line 30, after "Further" please insert -- , --.

Column 6,
Line 53, after "3'" please insert -- SEQ ID NO.1 --.

Signed and Sealed this

Fifth Day of November, 2002

Attest:

Attesting Officer

JAMES E. ROGAN
Director of the United States Patent and Trademark Office